United States Patent [19]

Binder et al.

[11] Patent Number: 5,500,201
[45] Date of Patent: Mar. 19, 1996

[54] METHOD OF TREATING CARBON BLACK AND CARBON BLACK SO TREATED

[75] Inventors: Michael Binder, Brooklyn, N.Y.; Robert J. Mammone, So Plainfield, N.J.

[73] Assignee: The United States of America as represented by the Secretary of the Army, Washington, D.C.

[21] Appl. No.: 343,805

[22] Filed: Nov. 22, 1994

[51] Int. Cl.⁶ ................................................ C09G 1/56
[52] U.S. Cl. .................... 423/449.2; 423/449.3; 423/449.4; 423/449.5
[58] Field of Search ............... 423/449.1, 449.4, 423/449.5, 449.3, 449.2; 264/22

[56] References Cited

U.S. PATENT DOCUMENTS 5,328,782  7/1994  Binder et al. ................ 429/232

FOREIGN PATENT DOCUMENTS 60-252663  12/1985  Japan ................... 423/449.5

*Primary Examiner*—Michael Lewis
*Assistant Examiner*—Stuart L. Hendrickson
*Attorney, Agent, or Firm*—Michael Zelenka; William H. Anderson

[57] ABSTRACT

The physical and chemical properties of carbon blacks are modified by exposing them to a room temperature gas plasma.

6 Claims, No Drawings

METHOD OF TREATING CARBON BLACK AND CARBON BLACK SO TREATED

GOVERNMENT INTEREST

The invention described herein may be manufactured, used, and licensed by or for the Government for governmental purposes without the payment to us of any royalty thereon.

FIELD OF INVENTION

This invention relates in general to a method of treating carbon black and to the carbon black so treated and in particular to a method of modifying the surface properties of carbon black and to the carbon black have the modified surface properties.

BACKGROUND OF THE INVENTION

Carbon blacks play a major role as a structural component, conductive support, and electrocatalyst support in batteries, double layer capacitors, and fuel cells. In addition, because of their unique physiochemical properties, including very high surface area and good electrical conductivity, they are widely used in the paint, tire and rubber industries as well as in gas filter applications.

It is well known that various surface functional groups present on the carbon, or deliberately anchored to the carbon after fabrication, play a significant role in deciding the ultimate physical and chemical properties of carbon blacks. Since it is possible to directly introduce appropriate electroactive functional groups (such as carboxyl, hydroxyl or quinone etc.) at carbon black surfaces via chemical, or thermal processes, the acid/base character or the hydrophobic/hydrophilic nature of carbon blacks can be changed. Although these methods can be used to change carbon black surface chemistry, they are time consuming, require complicated processing and often involve hazardous or toxic chemicals along with substantially increased manufacturing costs.

SUMMARY OF THE INVENTION

The general object of this invention is to provide a method of easily and inexpensively modifying the surface properties of carbon blacks. A more particular object of the invention is to provide such a method wherein the resulting carbon blacks with the modified properties can effectively be used in fuel cell systems, batteries, paint, rubber and tire industries, double layer capacitors, gas filters, and in a variety of chemical or electrochemical reactions where carbon is used as a catalyst support.

It has now been found that the aforementioned objects can be attained by exposing the carbon blacks to a room temperature gas plasma treatment to modify surface properties of the carbon black.

This gas plasma treatment, using selected gases, can modify carbon chemical groups, thereby changing physical and chemical properties of carbon black. These changes can have a definite influence on carbon black performance as a catalyst support in fuel cells and other chemical systems, double layer capacitors, porous cathodes in battery systems, gas filters and any application where carbon black is used.

DESCRIPTION OF THE PREFERRED EMBODIMENT

To treat carbon black by gas plasma, a dry carbon powder is placed in a chamber of a barrel plasma etcher. The chamber is evacuated by means of a vacuum pump, and back filled at a small flow rate with a selected gas. The gas can be an element such as oxygen, nitrogen, helium, chlorine or fluorine, or it may be a compound or mixtures of compounds such as ammonia, $NO_2$, NO or a mixture such as $CF_4/O_2$. When the rf power is turned on, the gas in the chamber dissociates, and the formed ions, radicals, and electrons react with carbon black surfaces. Because it is a gas phase reaction, the process is relatively rapid. Typical treatment times are less than 5 minutes. When the rf power is turned off, these gas phase reactive species recombine to form the original gas, and, since no hazardous products are formed, the gas can be safely vented to the atmosphere.

As illustrated in the Table, gas plasma treatment of carbon black can dramatically change the chemical nature of carbon blacks. The carbon black wettability increases by more than 5% and the pH changes by 3 pH units after exposure to a $CF_4/O_2$ gas plasma.

TABLE

Wettability and pH of carbon black powder after exposure to a $CF_4/O_2$ gas plasma.

| | WETTABILITY, ml | pH |
|---|---|---|
| BASELINE | 35.0 | 7.6 |
| $CF_4/O_2$ TREATED | 36.8 | 3.6 |

The carbon black treated is a finely divided form of carbon made by the incomplete combustion or thermal decomposition of natural gas or petroleum oil. The principal types, according to the method of production, are channel black, furnace black, and thermal black.

We wish it to be understood that we do not desire to be limited to the exact details of construction shown and described for obvious modifications will occur to a person skilled in the art.

What is claimed is:

1. Method of treating carbon black so as to modify its surface properties comprising exposing the carbon black to a room temperature gas plasma wherein the gas plasma is He.

2. Method of treating carbon black so as to modify its surface properties comprising exposing the carbon black to a room temperature gas plasma wherein the gas plasma is $Cl_2$.

3. Method of treating carbon black so as to modify its surface properties comprising exposing the carbon black to a room temperature gas plasma wherein the gas plasma is $F_2$.

4. Method of treating carbon black so as to modify its surface properties comprising exposing the carbon black to a room temperature gas plasma wherein the gas plasma is NO.

5. Method of treating carbon black so as to modify its surface properties, comprising exposing the carbon black to a room temperature gas plasma wherein the gas plasma is $CF_4$.

6. Method of treating carbon black so as to modify its surface properties comprising exposing the carbon black to a room temperature gas plasma wherein the gas plasma is $NO_2$.

* * * * *